United States Patent
Arnold et al.

(12)

(10) Patent No.: US 6,395,936 B1
(45) Date of Patent: May 28, 2002

(54) METHOD FOR THE CATALYTIC GAS PHASE OXIDATION OF PROPENE INTO ACROLEIN

(75) Inventors: Heiko Arnold; Signe Unverricht; Ulrich Hammon, all of Mannheim; Hans-Peter Neumann, Ludwigshafen; Klaus Harth, Altleiningen; Andreas Tenten, Maikammer, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/936,138

(22) PCT Filed: Feb. 28, 2000

(86) PCT No.: PCT/EP00/01634

§ 371 (c)(1),
(2), (4) Date: Sep. 10, 2001

(87) PCT Pub. No.: WO00/53556

PCT Pub. Date: Sep. 14, 2000

(30) Foreign Application Priority Data

Mar. 10, 1999 (DE) .......................................... 199 10 506
Oct. 7, 1999 (DE) .......................................... 199 48 241

(51) Int. Cl.[7] .......................... C07C 45/00; C07C 51/16
(52) U.S. Cl. .................. 568/476; 568/476; 568/449; 568/491; 568/480; 562/532; 562/534
(58) Field of Search ................ 568/476, 449, 568/491, 477, 480; 562/532, 534, 535

(56) References Cited

U.S. PATENT DOCUMENTS

| | | | |
|---|---|---|---|
| 4,203,906 A | 5/1980 | Takada et al. | |
| 4,298,763 A | 11/1981 | Engelbach et al. | |
| 4,365,087 A | 12/1982 | Kadowaki et al. | |
| 4,438,217 A | 3/1984 | Takata et al. | |
| 4,537,874 A | 8/1985 | Sato et al. | |
| 5,144,091 A | * 9/1992 | Martan et al. | |
| 5,364,825 A | 11/1994 | Neumann et al. | |
| 6,028,220 A | 2/2000 | Wada et al. | |

FOREIGN PATENT DOCUMENTS

| | | |
|---|---|---|
| DE | 25 13 405 | 10/1976 |
| DE | 30 02 829 | 7/1980 |
| DE | 33 00 044 | 7/1983 |
| DE | 33 38 380 | 10/1988 |
| DE | 28 30 765 | 6/1992 |
| DE | 198 55 913 | 8/2000 |
| EP | 0 015 565 | 9/1980 |
| EP | 0 253 409 | 1/1988 |
| EP | 0 257 565 | 3/1988 |
| EP | 0 279 374 | 8/1988 |
| EP | 0 293 224 | 11/1988 |
| EP | 0 450 596 | 10/1991 |
| EP | 0 575 897 | 12/1993 |
| EP | 0 700 714 | 3/1996 |
| EP | 0 807 465 | 11/1997 |
| EP | 0 900 774 | 3/1999 |
| JP | 3-294239 | 12/1991 |
| WO | WO 98/24746 | 6/1998 |

* cited by examiner

*Primary Examiner*—Gary Geist
*Assistant Examiner*—Farhad Forohar
(74) *Attorney, Agent, or Firm*—Oblon, Spivak, McClelland, Maier & Neustadt, P.C.

(57) ABSTRACT

In a process for the catalytic gas-phase oxidation of propene to acrolein, the reaction gas starting mixture is passed with a propene loading of $\geq 160$ l(S.T.P.)/l·h over a fixed-bed catalyst which is housed in two spatially successive reaction zones A,B, the reaction zone B being kept at a higher temperature than the reaction zone A.

27 Claims, No Drawings

METHOD FOR THE CATALYTIC GAS PHASE OXIDATION OF PROPENE INTO ACROLEIN

The present invention relates to a process for the catalytic gas-phase oxidation of propene to acrolein, in which a reaction gas starting mixture comprising propene, molecular oxygen and at least one inert gas, at least 20% by volume of which consists of molecular nitrogen, and containing the molecular oxygen and the propene in a molar ratio $O_2:C_3H_6$ of $\geq 1$ is passed over a fixed-bed catalyst, whose active material is at least one molybdenum- and/or tungsten- and bismuth-, tellurium-, antimony-, tin- and/or copper-containing multimetal oxide, in such a way that the propene conversion in a single pass is $\geq 90$ mol % and the associated selectivity of the acrolein formation and of the acrylic acid byproduct formation together is $\geq 90$ mol %.

The abovementioned process for the catalytic gas-phase oxidation of propene to acrolein is generally known (cf. for example EP-A 15565, EP-A 700714, DE-C 2830765, DE-C 3338380, JP-A 91/294239, EP-A 807 465, WO 98/24746, EP-B 279374, DE-C 2513405, DE-A 3300044, EP-A 575897 and DE-A 19855913) and is important in particular as the first oxidation stage in the preparation of acrylic acid by two-stage catalytic gas-phase oxidation of propene in two reaction stages in series (cf. for example DE A 3002829). Acrylic acid is an important monomer which is used as such or in the form of its alkyl esters for the production of polymers suitable, for example, as adhesives.

Since a small amount of acrylic acid byproduct is usually formed in the abovementioned catalytic gas-phase oxidation of propene to acrolein and, according to the above, acrylic acid is as a rule the desired natural secondary product of acrolein, the molar sum of acrolein formed and acrylic acid formed as byproduct is usually considered as desired product in a catalytic gas-phase oxidation of propene to acrolein. This approach is also to be applicable in the present patent application.

The object of any catalytic fixed-bed gas-phase oxidation of propene to acrolein is in principle to obtain a very high space-time yield (STY) of desired product (in a continuous procedure, this is the amount of desired product produced in grams per hour and unit volume of the catalyst bed used in liters).

There is therefore general interest in carrying out the gas-phase oxidation with a very high loading of the catalyst bed with propene (this is understood as meaning the amount of propene in liters under standard temperature and pressure conditions (=l(S.T.P.); the volume in liters which the corresponding amount of propene would assume under standard temperature and pressure conditions, i.e. at 25° C. and 1 bar) which is passed as a component of the reaction gas mixture, per hour, through one liter of catalyst bed), without significantly impairing the propene conversion taking place in a single pass of the reaction gas starting mixture through the catalyst bed and the selectivity of the associated formation of desired product.

The implementation of the abovementioned is impaired by the fact that gas-phase oxidation of propene to acrolein on the one hand is highly exothermic and on the other hand is accompanied by a multiplicity of possible parallel and subsequent reactions.

With increasing loading of the catalyst bed with propene, and with realization of the desired boundary condition of an essentially constant propene conversion, it must therefore be assumed that the selectivity of the formation of desired product decreases as a result of the greater heat production (cf. EP-B 450596, Example 1 and 2).

The conventional processes for the catalytic gas-phase oxidation of propene to acrolein, wherein nitrogen is used as a main component of the inert diluent gas and in addition a fixed-fed catalyst present in a reaction zone and homogeneous along this reaction zone, i.e. having a chemically uniform composition over the catalyst bed, is employed and the temperature of the reaction zone is kept at a value standard over the reaction zone (temperature of the reaction zone here is understood as meaning the temperature of the catalyst bed present in the reaction zone when the process is carried out in the absence of a chemical reaction; if this temperature in such reaction zone is not constant, the term temperature of the reaction zone means here the numerical average of the temperature of the catalyst bed along the reaction zone), therefore limit the applicable value of the propene loading of the catalyst bed to $\leq 155$ l(S.T.P.) of propene per l of catalyst bed per h (cf. for example EP-A 15565 (maximum propene load=120 l(S.T.P.) of propene/l·h), DE-C 2830765 (maximum propene load=94.5 l(S.T.P.) of propene/l·h), EP-A 804465 (maximum propene load=128 l(S.T.P.) of propene/l·h), EP-B 279374 (maximum propene load=112 l(S.T.P.) of propene/l·h), DE-C 2513405 (maximum propene load=110 l(S.T.P.) of propene/l·h), DE-A 3300044 (maximum propene load=112 l(S.T.P.) of propene/l·h), EP-A 575897 (maximum propene load=120 l(S.T.P.) of propene/l·h), DE-C 3338380 (in essentially all examples, the maximum propene load is 126 l(S.T.P.) of propene/l·h; only in the case of a special catalyst composition was a propene load of 162 l(S.T.P.)/l·h realized) and DE-A 19855913 (maximum propene load=155 l(S.T.P.) of propene/l·h)).

WO 98/24746 considers it necessary, even at a propene loading of up to 148.8 l(S.T.P.) of propene/l·h, to structure the catalyst bed in such a way that its volume-specific activity increases gradually in the direction of flow of the reaction gas mixture.

Although JP-A 91/294239 discloses, in an exemplary embodiment, that a propene load of the catalyst bed with 160 l(S.T.P.) of propene/l·h is possible in an essentially conventional procedure for a catalytic gas-phase oxidation of propene to acrolein, this is likewise only at the expense of a volume-specific activity gradually increasing in the direction of flow of the reaction gas mixture. However, such a procedure is not very practicable on an industrial scale, the gas-phase catalytic oxidation of propene to acrolein usually being carried in tube-bundle reactors comprising a few thousand catalyst tubes, each individual one of which has to be loaded with a gradated catalyst bed.

EP-B 253409 and the associated equivalent, EP-B 257565, disclose that, with the use of an inert diluent gas which has a higher molar heat capacity than molecular nitrogen, the propene content of the reaction gas starting mixture can be increased. Nevertheless, in the two abovementioned publications, the maximum realized propene loading of the catalyst bed is 140 l(S.T.P.) of propene/l·h.

Only in EP-A 293224 have propene loadings above 160 l(S.T.P.) of propene/l·h been realized to date. However, this has been achieved at the expense of a special inert diluent gas to be used, which is completely free of molecular nitrogen. The disadvantage of this diluent gas is in particular the fact that, in contrast to molecular nitrogen, all its components are desired products which, when the process is carried out continuously, have to be recycled at least partially to the gas-phase oxidation in an expensive manner for cost-efficiency reasons.

EP-B 450596 used a structured bed of catalyst and obtained a propene loading of 202.5 l(S.T.P)/l·h, but at the cost of reduced selectivity to desired product.

It is an object of the present invention to provide a process, as defined at the outset, for the catalytic gas-phase oxidation of propene to acrolein, which process ensures a higher space-time yield with respect to desired product without having the disadvantages of the high-load procedures of the prior art.

We have found that this object is achieved by a process for the catalytic gas-phase oxidation of propene to acrolein, in which a reaction gas starting mixture comprising propene, molecular oxygen and at least one inert gas, at least 20% by volume of which consists of molecular nitrogen, and containing the molecular oxygen and the propene in a molar ratio $O_2:C_3H_6$ of $\geq 1$ is passed, at elevated temperatures, over a fixed-bed catalyst, whose active material is at least one molybdenum- and/or tungsten- and bismuth-, tellurium-, antimony-, tin- and/or copper- (preferably at least one Mo-, Bi- and Fe-)containing multimetal oxide, in such a way that the propene conversion in a single pass is $\geq 90$ mol % and the associated selectivity of the acrolein formation and of the acrylic acid byproduct formation together is $\geq 90$ mol %, wherein a) the loading of the fixed-bed catalyst with the propene contained in the reaction gas starting mixture is $\geq 160$ l(S.T.P.) of propene per 1 of catalyst bed per h, b) the fixed-bed catalyst consists of a catalyst bed arranged in two spatially successive reaction zones A, B, the temperature of the reaction zone A being from 300 to 390° C. (frequently to 350° C.) and the temperature of the reaction zone B being from 305 to 4200° C. (frequently up to 380° C.) and at the same time being at least 5° C. above the temperature of the reaction zone A, c) the reaction gas starting mixture flows first through the reaction zone A and then through the reaction zone B and d) the reaction zone A extends to a propene conversion of from 40 to 80 mol %.

Preferably, the reaction zone A extends to a propene conversion of from 50 to 70, particularly preferably from 65 to 75, mol %.

According to the invention, the temperature of the reaction zone B is advantageously from 305 to 365° C., or 340° C., particularly advantageously from 310 to 3300° C.

Furthermore, the temperature of the reaction zone B is preferably at least 10° C. above the temperature of the reaction zone A.

The higher the chosen propene loading of the catalyst bed in the novel process, the greater should be the chosen difference between the temperature of the reaction zone A and the temperature of the reaction zone B. Usually, however, the abovementioned temperature difference in the novel process will be not more than 50° C., i.e. the difference between the temperature of the reaction zone A and the temperature of the reaction zone B may be, according to the invention, up to 20° C., up to 25° C., up to 30° C., up to 40° C., up to 45° C. or up to 50° C.

As a rule, the propene conversion, based on the one pass, in the novel process is $\geq 92$ mol % or $\geq 94$ mol %. The selectivity of the formation of desired product is usually $\geq 92$ mol % or $\geq 94$ mol %, frequently $\geq 95$ mol % or $\geq 96$ mol % or $\geq 97$ mol %.

Surprisingly, the abovementioned applies not only in the case of propene loadings of the catalyst bed of $\geq 165$ l(S.T.P.)/l·h or of $\geq 170$ l(S.T.P.)/l·h or $\geq 175$ l(S.T.P.)/l·h or $\geq 180$ l(S.T.P.)/l·h, but also in the case of propene loadings of the catalyst bed of >20 185 l(S.T.P.)/l·h or $\geq 190$ l(S.T.P.)/l·h or $\geq 200$ l(S.T.P.)/l·h or $\geq 210$ l(S.T.P.)/l·h and in the case of loadings of $\geq 220$ l(S.T.P.)/l·h or $\geq 230$ l(S.T.P.)/l·h or $\geq 240$ l(S.T.P.)/l·h or >250 l(S.T.P.)/l·h.

In this respect, it is surprising that the abovementioned values are achievable even when the inert gas used according to the invention comprises $\geq 30\%$ by volume or $\geq 40\%$ by volume or $\geq 50\%$ by volume or $\geq 60\%$ by volume or $\geq 70\%$ by volume or $\geq 80\%$ by volume or $\geq 90\%$ by volume or $\geq 95\%$ by volume of molecular nitrogen. In the case of propene loadings above 250 l(S.T.P.)/l·h, the presence of inert (inert diluent gases are intended in general to be those which undergo less than 5%, preferably less than 2%, conversion during a single pass) diluent gases such as propane, ethane, methane, pentane, butane, $CO_2$, CO, steam and/or noble gases, is recommended for the novel process. However, these gases and their mixtures can of course also be used in the case of lower loadings and as sole diluent gases. It is furthermore surprising that the novel process can be carried out using a catalyst bed which is homogeneous, i.e. chemically uniform, over both reaction zones, without suffering significant declines in the conversion and/or in selectivity.

In the novel process, the propene loading usually will not exceed 600 l(S.T.P.)/l·h. In the novel process, without significant loss of conversion and selectivity, the propene loadings are typically $\leq 30$, frequently $\leq 25$, l(S.T.P.)/l·h.

In the novel process, the operating pressure may be either below atmospheric pressure (for example up to 0.5 bar) or above atmospheric pressure. Typically, the operating pressure is from 1 to 5 bar, frequently from 1.5 to 3.5, bar. Usually, the reaction pressure will not exceed 100 bar.

According to the invention, the molar $O_2:C_3H_6$ ratio in the reaction gas starting mixture must be $\geq 1$. Usually, this ratio is $\leq 3$. According to the invention, the molar $O_2:C_3H_6$ ratio in the reaction gas starting mixture is frequently $\geq 1.5$ and $\leq 2.0$.

A suitable source of the molecular oxygen required in the novel process is air as well as air depleted in molecular nitrogen (for example $\geq 90\%$ by volume Of $O_2$ and $\leq 10\%$ by volume of $N_2$).

According to the invention, the propene content of the reaction gas starting mixture may be, for example, from 4 to 15, frequently from 5 to 12, % by volume or from 5 to 8% by volume (based in each case on the total volume).

Frequently, the novel process is carried out at a volume ratio of propene to oxygen to inert gases (including steam) in the reaction gas starting mixture of 1:(1.0 to 3.0):(5 to 25), preferably 1:(1.7 to 2.3):(10 to 15).

Usually, the reaction gas starting mixture contains essentially no further components apart from said constituents.

Suitable fixed-bed catalysts for the novel process are all those whose active material is at least one Mo-, Bi- and Fe-containing multimetal oxide.

This means in principle that all those catalysts which are disclosed in DE-C 3338380, DE-A 19902562, EP-A 15565, DE-C 2830765, EP-A 807465, EP-A 279374, DE-A 3300044, EP-A 575897, U.S. Pat. No. 4438217, DE-A 19855913, WO 98/24746, DE-A 19746210 (those of the formula II), JP-A 91/294239, EP-A 293224 and EP-A 700714 can be used according to the invention. This applies in particular to the exemplary embodiments in these publications, among which those of EP-A 15565, of EP-A 575897, of DE-A 19746210 and of DE-A 19855913 are particularly preferred. A catalyst according to Example 1c of EP-A 15565 and a catalyst which is to be prepared in a corresponding manner but whose active material has the composition $Mo_{12}Ni_{6.5}Zn_2Fe_2Bi_1P_{0.0065}K_{0.06}O_x \cdot 10SiO_2$ are particularly noteworthy in this context. The example with the consecutive No. 3 from DE-A 19855913 (stoichiometry: $Mo_{12}Co_7 Fe_3 Bi_{0.6}K_{0.08}Si_{1.6}O_x$) as an unsupported catalyst in the form of hollow cylinders and measuring 5 mm×3 mm×2 mm (external diameter×height×internal diameter) and the unsupported multimetal oxide II catalyst according to Example 1 of DE-A 19746210 are also noteworthy. The multimetal oxide catalysts of U.S. Pat. No. 4438217 should also be mentioned. The latter applies in particular when these hollow cylinders measure 5 mm×2 mm×2 mm or 5 mm×3 mm×2 mm or 6 mm×3mm×3mm or 7 mm×3mm×4 mm (in each case external diameter×height×internal diameter).

A multiplicity of the multimetal oxide active materials suitable according to the invention can be subsumed under the formula I $$Mo_{12}Bi_aFe_bX_c^1X_d^2X_e^3X_f^4O_n \qquad (I),$$

where
- $X^1$ is nickel and/or cobalt,
- $X^2$ is thallium, an alkali metal and/or an alkaline earth metal,
- $X^3$ is zinc, phosphorus, arsenic, boron, antimony, tin, cerium, lead and/or tungsten,
- $X^4$ is silicon, aluminum, titanium and/or zirconium,
- a is from 0.5 to 5,
- b is from 0.01 to 5, preferably from 2 to 4,
- c is from 0 to 10, preferably from 3 to 10,
- d is from 0 to 2, preferably from 0.02 to 2,
- e is from 0 to 8, preferably from 0 to 5,
- f is from 0 to 10 and
- n is a number which is determined by the valency and frequency of the elements in I other than oxygen.

They are obtainable in a manner known per se (cf. for example DE-A 4023239) and are usually molded as such into spheres, rings or cylinders or used in the form of coated catalysts, i.e. premolded inert carriers coated with the active material. However, they can of course also be used in powder form as catalysts. According to the invention, it is of course also possible to use the Bi-, Mo- and Fe-comprising multimetal oxide catalyst ACS-4 from Nippon Schokubai.

In principle, active materials suitable according to the invention, in particular those of the formula I, can be prepared in a simple manner by producing, from suitable sources of their elemental constituents, a very intimate, preferably finely divided dry blend having a composition corresponding to their stoichiometry and calcining said dry blend at from 350 to 650° C. The calcination can be carried out either under inert gas or under an oxidizing atmosphere, e.g. air (mixture of inert gas and oxygen) or under a reducing atmosphere (for example, a mixture of inert gas, $NH_3$, CO and/or $H_2$). The duration of calcination may be from a few minutes to a few hours and usually decreases with increasing temperature. Suitable sources of the elemental constituents of multimetal oxide active materials I are those compounds which are already oxides and/or those compounds which can be converted into oxides by heating, at least in the presence of oxygen.

In addition to the oxides, suitable starting compounds of this type are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be decomposed, at the latest during the subsequent calcination, into compounds which escape completely in gaseous form, may additionally be incorporated into the intimate dry blend).

The thorough mixing of the starting compounds for the preparation of multimetal oxide materials I can be effected in dry or in wet form. If it is carried out in dry form, the starting compounds are expediently used in the form of finely divided powders and, after mixing and any compaction, are subjected to calcination. However, the thorough mixing is preferably effected in wet form. Usually, the starting compounds are mixed with one another in the form of an aqueous solution and/or suspension. Particularly intimate dry blends are obtained in the mixing method described when exclusively sources of the elemental constituents in solution are used as starting materials. A preferably used solvent is water. The aqueous material obtained is then dried, the drying process preferably being carried out by spray-drying the aqueous mixture with outlet temperatures of from 100 to 150° C.

The multimetal oxide materials suitable according to the invention, in particular those of the formula I, can be used for the novel process both in powder form and after molding to give specific catalyst geometries, it being possible to carry out the shaping before or after the final calcination. For example, unsupported catalysts can be prepared from the powder form of the active material or its uncalcined and/or partially calcined precursor material by compaction to give the desired catalyst geometry (for example by pelleting or extrusion), it being possible to add assistants, such as graphite or stearic acid as lubricants and/or molding assistants and reinforcing agents, such as microfibers of glass, asbestos, silicon carbide or potassium titanate. Suitable unsupported catalyst geometries are, for example, solid cylinders or hollow cylinders having an external diameter and a length of from 2 to 10 mm. In the case of hollow cylinders, a wall thickness of from 1 to 3 mm is expedient. The unsupported catalyst may of course also have spherical geometry, it being possible for the sphere diameter to be from 2 to 10 mm.

The shaping of the pulverulent active material or of its pulverulent, still uncalcined and/or partially calcined precursor material can of course also be effected by application to premolded inert catalyst carriers. The coating of the carriers for the preparation of the coated catalysts is carried out, as a rule, in a suitable rotatable container, as disclosed, for example, in DE-A 2909671, EP-A 293859 or EP-A 714700. For coating the carriers, the powder material to be applied is expediently moistened and, after application, is dried again, for example by means of hot air. The coat thickness of the powder material applied to the carrier is expediently chosen to be from 10 to 1000 μm, preferably from 50 to 500 μm, particularly preferably from 150 to 250 μm.

Conventional porous or nonporous aluminas, silica, thorium dioxide, zirconium dioxide, silicon carbide or silicates, such as magnesium silicate or aluminum silicate, can be used as carrier materials. The carriers may have a regular or irregular shape, those having a regular shape and substantial surface roughness, for example spheres or hollow cylinders, being preferred. The use of essentially nonporous, spherical steatite carriers which have a rough surface and whose diameter is from 1 to 8 mm, preferably from 4 to 5 mm, is suitable. However, the use of cylinders whose length is from 2 to 10 mm and whose external diameter is from 4 to 10 mm as carriers is also suitable. In the case of rings suitable according to the invention as carriers, the wall thickness is moreover usually from 1 to 4 mm. Annular carriers preferably to be used according to the invention have a length of from 3 to 6 mm, an external diameter of from 4 to 8 mm and a wall thickness of from 1 to 2 mm. Rings measuring 7 mm×3mm×4 mm (external diameter×length×internal diameter) are also particularly suitable according to the invention as carriers. The fineness of the catalytically active oxide materials to be applied to the surface of the carrier is of course adapted to the desired coat thickness (cf. EP-A 714 700).

Advantageous multimetal oxide active materials to be used according to the invention are furthermore materials of the formula II

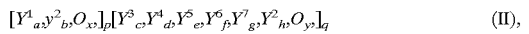

where

Y¹ is bismuth, tellurium, antimony, tin and/or copper,

Y² is molybdenum and/or tungsten,

Y³ is an alkali metal, thallium and/or samarium,

Y⁴ is an alkaline earth metal, nickel, cobalt, copper, manganese, zinc, tin, cadmium and/or mercury, Y⁵ is iron, chromium, cerium and/or vanadium, Y⁶ is phosphorus, arsenic, boron and/or antimony, and Y⁷ is a rare earth metal, titanium, zirconium, niobium, tantalum, rhenium, ruthenium, rhodium, silver, gold, aluminum, gallium, indium, silicon, germanium, lead, thorium and/or uranium, a' is from 0.01 to 8,
b' is from 0.1 to 30,
c' is from 0 to 4,
d' is from 0 to 20,
e' is from 0 to 20,
f' is from 0 to 6,
g' is from 0 to 15,
h' is from 8 to 16,
x',y' are numbers which are determined by the valency and frequency of the elements in II other than oxygen and
p,q are numbers whose ratio p/q is from 0.1 to 10, containing three-dimensional regions of the chemical composition $Y^1_{a'}Y^2_{b'}O_{x'}$, which, owing to their composition differing from their local environment, are delimited with respect to their local environment and whose maximum diameter (longest distance between two points present on the surface (interface) of the region and passing through the center of gravity of the region) is from 1 nm to 100 μm, frequently from 10 nm to 500 nm or from 1 μm to 50 or 25 μm.

Particularly advantageous novel multimetal oxide materials II are those in which Y¹ is bismuth.

Preferred among these in turn are those which are of the formula III

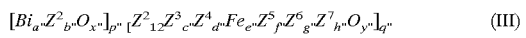

where

Z² is molybdenum and/or tungsten,
Z³ is nickel and/or cobalt,
Z⁴ is thallium, an alkali metal and/or an alkaline earth metal,
Z⁵ is phosphorus, arsenic, boron, antimony, tin, cerium and/or lead,
Z⁶ is silicon, aluminum, titanium and/or zirconium,
Z⁷ is copper, silver and/or gold,
a" is from 0.1 to 1,
b" is from 0.2 to 2,
c" is from 3 to 10,
d" is from 0.02 to 2,
e" is from 0.01 to 5, preferably from 0.1 to 3,
f" is from 0 to 5,
g" is from 0 to 10,
h" is from 0 to 1,
x",y" are numbers which are determined by the valency and frequency of the elements in III other than oxygen and
p",q" are numbers whose ratio p"/q" is from 0.1 to 5, preferably from 0.5 to 2, very particularly preferred materials III being those in which $Z^2_{b"}$ is (tungsten)$_{b"}$ and $Z^2_{12}$ is (molybdenum)$_{12}$.

It is furthermore advantageous if at least 25 mol % (preferably at least 50, particularly preferably at least 100, mol %) of the total amount $[Y^1_{a'}Y^2_{b'}O_{x'}]_p$ ($[Bi_{a"}Z^2_{b"}O_{x"}]_{p"}$) of the multimetal oxide materials II (multimetal oxide materials III) suitable according to the invention are present in the multimetal oxide materials II (multimetal oxide materials III) suitable according to the invention in the form of three-dimensional regions of the chemical composition $Y^1_{a'}$, $Y^2_{b'}O_{x'}$, $[Bi_{a"}Z^2_{b"}O_{x"}]$ which, owing to their chemical composition differing from their local environment, are delimited with respect to their local environment and whose maximum diameter is from 1 nm to 100 μm.

Regarding the shaping, the statements made with respect to the catalysts comprising multimetal oxide materials I are applicable to catalysts comprising multimetal oxide materials II.

The preparation of active materials from multimetal oxide materials II is described, for example, in EP-A 575897 and in DE-A 19855913.

In a manner expedient in terms of application technology, the novel process is carried out in a two-zone tube-bundle reactor. A preferred variant of a two-zone two-bundle reactor which can be used according to the invention is disclosed in DE-C 2830765. However, the two-zone tube-bundle reactors disclosed in DE-C 2513405, U.S. Pat. No. 3147084, DE-A 2201528 and DE-A 2903218 are also suitable for carrying out the novel process.

This means that, in the simplest procedure, the fixed-bed catalyst to be used according to the invention is present in the metal tubes of a tube-bundle reactor, and two heating media, as a rule salt melts, essentially spatially separated from one another, are passed around the metal tubes. The tube section over which the respective salt bath extends represents, according to the invention, a reaction zone, i.e. in the simplest procedure a salt bath A flows around that section of the tubes (the reaction zone A) in which the oxidative reaction of the propene (in a single pass) takes place until a conversion of from 40 to 80 mol % is reached, and a salt bath B flows around that section of the tubes (the reaction zone B) in which the subsequent oxidative reaction of the propene (in a single pass) takes place until a conversion of at least 90 mol % is reached (if required, further reaction zones which are kept at individual temperatures may follow the reaction zones A, B to be used according to the invention).

It is expedient in terms of application technology if the novel process comprises no further reaction zone, i.e. the salt bath B expediently flows around that section of the tubes in which the subsequent oxidative reaction of the propene (in a single pass) takes place up to a conversion of ≧92 mol % or ≧94 mol % or more.

Usually, the beginning of the reaction zone B is behind the hot-spot maximum of the reaction zone A. The hot-spot maximum of the reaction zone B is usually below the hot-spot maximum temperature of the reaction zone A.

According to the invention, the two salt baths A, B can be passed cocurrent or countercurrent through the space surrounding the reaction tubes, relative to the direction of flow of the reaction gas mixture flowing through the reaction tubes. According to the invention, it is of course also possible to employ cocurrent flow in the reaction zone A and countercurrent flow in the reaction zone B (or vice versa).

In all abovementioned configurations, it is of course also possible to superpose a transverse flow on the flow of the salt melt parallel to the reaction tubes, within the respective reaction zone, so that the individual reaction zone corresponds to a tube-bundle reactor as described in EP-A 700714 or in EP-A 700893 and a meandering flow of the heat exchange medium results through the catalyst tube bundle in the longitudinal section as a whole.

Expediently, the reaction gas starting mixture is preheated to the reaction temperature before being fed to the catalyst bed.

In the abovementioned tube-bundle reactors, the catalyst tubes are usually produced from ferritic steel and typically have a wall thickness of from 1 to 3 mm. Their internal diameter is as a rule from 20 to 30 mm, frequently from 22 to 26 mm. It is expedient in terms of application technology if the number of catalyst tubes housed in the tube-bundle container is at least 5000, preferably at least 10,000. Frequently, the number of catalyst tubes housed in the reaction container is from 15,000 to 30,000. Tube-bundle reactors having more than 40,000 catalyst tubes tend to be the exception. Inside the container, the catalyst tubes are usually homogeneously distributed, the distribution expediently being chosen so that the distance between the central inner axes of adjacent catalyst tubes (the catalyst tube spacing) is from 35 to 45 mm (cf. for example EP-B 468290).

Particularly suitable heat exchange media are fluid heating media. The use of melts of salts such as potassium nitrate, potassium nitrite, sodium nitrite and/or sodium nitrate or of metals having a low melting point, such as sodium, mercury or alloys of various metals, is particularly advantageous.

In all abovementioned configurations of the flow in the two-zone tube-bundle reactors, the flow rate inside the two required circulations of heat exchange medium is as a rule chosen so that the temperature of the heat exchange medium increases by from 0 to 15° C. from the point of entry into the reaction zone to the point of exit from the reaction zone, i.e. the abovementioned ΔT may be, according to the invention, from 1 to 10° C., or from 2 to 8° C. or from 3 to 6° C.

The temperature of the heat exchange medium on entry into the reaction zone A is, according to the invention, usually from 300 to 350° C. According to the invention, the temperature of the heat exchange medium on entry into the reaction zone B is usually, on the one hand, from 305 to 380° C. and, on the other hand, is simultaneously at least 5° C. above the temperature of the heat exchange medium entering the reaction zone A.

The temperature of the heat exchange medium on entry into the reaction zone B is preferably at least 10° C. above the temperature of the heat exchange medium entering the reaction zone A. The difference between the temperatures on entry into the reaction zones A and B may thus be, according to the invention, up to 20° C., up to 25° C., up to 30° C., up to 40° C., up to 45° C. or up to 50° C. Usually, however, the abovementioned temperature difference is not more than 50° C. The higher the chosen propene loading of the catalyst bed during the novel process, the greater should be the difference between the temperature of the heat exchange medium on entry into the reaction zone A and the temperature of the heat exchange medium on entry into the reaction zone B.

Advantageously, the temperature of the heat exchange medium on entry into the reaction zone B is, according to the invention, from 305 to 365° C. or 340° C., particularly advantageously from 310 to 330° C.

In the novel process, the two reaction zones A, B can of course also be realized in tube-bundle reactors spatialy separated from one another. If required, a heat exchanger may also be mounted between the two reaction zones. The two reaction zones A, B can of course also be designed as a fluidized bed.

In the novel process, it is also possible to use catalyst beds whose volume-specific activity in the direction of flow of the reaction mixture increases continuously, abruptly or stepwise (this can be effected as described in WO 98/24746 or in JP-A 91/294239 or by dilution with inert material). Moreover, the inert diluent gases (for example only propane or only methane etc.) recommended in EP-A 293224 and in EP-B 257565 can also be used for the two-zone procedure described. The latter can, if required, also be combined with a volume-specific activity of the catalyst bed which increases in the direction of flow of the reaction gas mixture.

It should once again be pointed out here that, for carrying out the novel process, it is also possible to use in particular the two-zone tube-bundle reactor type which is described in German published application DAS 2,201,528 and includes the possibility of transferring a portion of the hotter heat exchange medium of the reaction zone B to the reaction zone A in order, if required, to heat up a cold reaction gas starting mixture or a cold recycle gas.

The novel process is particularly suitable for being carried out continuously. It is surprising that it permits the higher space-time yield in the formation of the desired product in a single pass without at the same time significantly impairing the selectivity of the formation of the desired product. Rather, a nonsignificantly higher selectivity in the formation of the desired product is even observed.

The latter is presumably due to the fact that, owing to the higher temperatures present in the region of higher propene conversion, the novel process results in less readsorption of the resulting acrolein onto the fixed-bed catalyst.

It is also noteworthy that the catalyst life in the novel process is completely satisfactory in spite of the extreme loading of the catalyst with the reactants.

The novel process does not give pure acrolein but a mixture from whose secondary components the acrolein can be separated off in a manner known per se. Unconverted propene and inert diluent gas used and/or formed in the course of the reaction can be recycled to the gas-phase oxidation. When acrolein is used for the preparation of acrylic acid by two-stage catalytic gas-phase oxidation of propene, the acrolein-containing reaction gases are transferred to the second oxidation stage as a rule without removal of the secondary components. If required, the novel two-zone procedure can of course also be used in the case of conventional propene loads.

Otherwise, conversion, selectivity and residence time are defined as follows in this publication, unless stated otherwise:

$$\text{Conversion } C_P \text{ of propene (\%)} = \frac{\text{Number of moles of propene converted}}{\text{Number of moles of propene used}} \times 100$$

$$\text{Selectivity } S_A \text{ of the acrolein formation (\%)} = \frac{\text{Number of moles of propene converted into acrolein}}{\text{Number of moles of propene converted}} \times 100$$

$$\text{Selectivity } S_{AS} \text{ of the formation of acrylic acid byproduct (\%)} = \frac{\text{Number of moles of propene converted into acrylic acid}}{\text{Number of moles of propene converted}} \times 100$$

$$\text{Selectivity } S_{DP} \text{ of the formation of the desired product (\%)} = \frac{\text{Number of moles of propene converted into acrolein and into acrylic acid}}{\text{Number of moles of propene converted}} \times 100$$

$$\text{Residence time (sec)} = \frac{\text{Empty reactor volume filled with catalyst (l)}}{\text{Throughput of reaction gas starting mixture (l/h)}} \times 3600$$

EXAMPLES a) Catalyst Preparation

1. Preparation of a Starting Material 1

209.3 kg of tungstic acid (72.94% by weight of W) were stirred, a little at a time at 25° C., into 775 kg of an aqueous solution of bismuth nitrate in nitric acid (11.2% by weight of Bi, free nitric acid from 3 to 5% by weight; density: from 1.22 to 1.27 g/ml). The resulting aqueous mixture was then stirred for a further 2 hours at 25° C. and then spray-dried.

The spray-drying was carried out in a rotating-disk spray tower by the countercurrent method at a gas inlet temperature of 300±10° C. and a gas outlet temperature of 100±10° C. The spray-dried powder obtained was then calcined at from 780 to 810° C. (in a rotary tubular furnace through which air flowed (1.54 m$^3$ internal volume, 200 m$^3$ (S.T.P.) of air/h)). When establishing the exact calcination temperature, it is important that it is tailored to the desired phase composition of the calcination product. The phases WO$_3$ (monoclinic) and Bi$_2$W$_2$O$_9$ are desired, and the presence of $\gamma$-Bi$_2$WO$_6$ (russellite) is undesired. If, therefore, the compound $\gamma$-Bi$_2$WO$_6$ is still detectable after calcination on the basis of reflection at an angle of 2$\Theta$=28.4° (CuK$\alpha$ radiation) in the powder X-ray diffraction pattern, the preparation should be repeated and the calcination temperature increased within the stated temperature range until the reflection disappears. The preformed calcined mixed oxide obtained in this manner was milled so that the X$_{50}$ value (cf. Ullmann's Encyclopedia of Industrial Chemistry, 6th Edition (1998) Electronic Release, section 3.1.4 or DIN 66141) of the resulting particle size distribution was 5 $\mu$m. The milled material was then mixed with 1% by weight (based on the milled material) of finely divided SiO$_2$ (bulk density 150 g/l; X$_{50}$ value of the SiO$_2$ particles was 10 $\mu$m, the BET surface area was 100 m$^2$/g).

2. Preparation of a Starting Material 2

A solution A was prepared by dissolving 213 kg of ammonium heptamolybdate in 600 l of water at 60° C. while stirring, and adding 0.97 kg of an aqueous potassium hydroxide solution (46.8% by weight of KOH) at 20° C. to the resulting solution while maintaining the 60° C. and stirring.

A solution B was prepared by introducing 116.25 kg of an aqueous iron nitrate solution (14.2% by weight of Fe) into 262.9 kg of an aqueous cobalt nitrate solution (12.4% by weight of Co) at 60° C. The solution B was then pumped continuously over a period of 30 minutes into the initially taken solution A while maintaining the 60° C. Stirring was then carried out for 15 minutes at 60° C. Thereafter, 19.16 kg of a silica gel (46.80% by weight of SiO$_2$, density: from 1.36 to 1.42 g/ml, pH from 8.5 to 9.5, alkali metal content not more than 0.5% by weight) were added to the resulting aqueous mixture and stirring was then carried out for a further 15 minutes at 60° C.

Spray drying was then carried out in a rotating-disk spray tower by the countercurrent method (gas inlet temperature: 400±10° C., gas outlet temperature: 140±5° C.). The resulting spray-dried powder had a loss on ignition of about 30% by weight (calcining for 3 hours at 600° C.).

3. Preparation of the Multimetal Oxide Active Material

The starting material 1 was homogeneously mixed with the starting material 2 in the amount required for a multimetal oxide active material having a stoichiometry

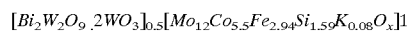

$[Bi_2W_2O_9 \cdot 2WO_3]_{0.5}[Mo_{12}Co_{5.5}Fe_{2.94}Si_{1.59}K_{0.08}O_x]1$

In addition, 1.5% by weight, based on the abovementioned total material, of finely divided graphite (sieve analysis: min. 50% by weight <24 μm. max. 10% by weight >24 μm and <48 μm, max. 5% by weight <48 μm, BET surface area: from 6 to 13 m$^2$/g) were mixed in homogeneously. The resulting dry blend was molded to give hollow cylinders having a length of 3 mm, an external diameter of 5 mm and a wall thickness of 1.5 mm and then subjected to a thermal treatment as follows.

In a muffle furnace through which air flowed (60 l internal volume, 1 l/h of air per gram of active precursor material), heating was effected at a heating rate of 180° C./h, initially from room temperature (25° C.) to 190° C. This temperature was maintained for 1 hour and then increased to 210° C. at a heating rate of 60° C./h. The 210° C. were in turn maintained for 1 hour before being increased at a heating rate of 60° C./h, to 230° C. This temperature was likewise maintained for 1 hour before it was increased to 265° C., once again at a heating rate of 60° C./h. The 265° C. were then likewise maintained for 1 hour. Thereafter, cooling to room temperature was initially effected, thus essentially completing the decomposition phase. Thereafter, heating was effected to 465° C. at a heating rate of 180° C./h, and this calcination temperature was maintained for 4 hours.

The resulting unsupported catalyst rings were used for the catalytic gas-phase propene oxidation described below.

b) Gas-phase Catalytic Oxidation of Propene to Acrolein

1. Loading of the Reaction Tube

A reaction tube (V2A stainless steel; 30 mm external diameter; 2 mm wall thickness; 26 mm internal diameter; length: 439 cm, having a tube (4 mm external diameter) centered in the center of the reaction tube and suitable for holding a thermocouple with which the temperature in the reaction tube could be determined) was loaded, on a catalyst support ledge (44 cm long), from bottom to top, initially over a length of 30 cm with steatite beads having a rough surface (from 4 to 5 mm diameter; inert material for heating the reaction gas starting mixture) and then over a length of 300 cm with the unsupported catalyst rings prepared in a), before the loading was completed over a length of 30 cm with the abovementioned steatite beads as a subsequent bed. The remaining 35 cm of catalyst tube were left empty.

That part of the reaction tube which had been loaded with solid was themostated by means of 12 aluminum blocks each 30 cm long, which were cast cylindrically around the tube and were heated by electric heating tapes (comparative experiments using a corresponding reaction tube heated by means of a salt bath through which nitrogen was bubbled showed that the thermostating by means of aluminum blocks was capable of simulating thermostating by means of a salt bath. The first six aluminum blocks in the direction of flow defined a reaction zone A and the remaining six aluminum blocks defined a reaction zone B. Those ends of the reaction tube which were free of solid were kept at 220° C. by means of steam under superatmospheric pressure.

The reaction tube described above was fed continuously with a reaction gas starting mixture of the following composition, the loading and the thermostating of the reaction tube being varied:

from 6 to 6.5% by volume of propene, from 3 to 3.5% by volume of H$_{2O,}$ from 0.3 to 0.5% by volume of CO, from 0.8 to 1.2% by volume of CO$_2$, from 0.025 to 0.04% by volume of acrolein, from 10.4 to 10.7% by volume of O$_2$, the remaining amount to 100% being molecular nitrogen (oxygen source was air, apart from a low O$_2$ content of the recycle gas)

A small sample for gas chromatographic analysis was taken from the product gas mixture at the reaction tube exit. Otherwise, the product gas mixture was fed directly into a downstream acrolein oxidation stage (to give acrylic acid). The acrylic acid was separated from the product gas mixture of the acrolein oxidation stage in a manner known per se, and a part of the remaining residual gas was reused for feeding the propene oxidation stage (as recycle gas), which explains the acrolein content of the abovementioned feed gas and the small variation in the feed composition.

The pressure at the reaction tube entrance varied, as a function of the chosen propene loading, in the range from 3.0 to 1.9 bar. An analysis point was likewise present at the end of the reaction zone A.

The results obtained depending on the chosen propene loading and on the chosen aluminum thermostating are shown in Table 1 below.

$T_A$ is the temperature of the aluminum blocks in the reaction zone A and $T_B$ is the temperature of the aluminum blocks in the reaction zone B.

$U_{PA}$ is the propene conversion at the end of the reaction zone A and CPE is the propene conversion at the reaction tube exit. $S_{AE}$, $S_{AAE}$ and $S_{DPE}$ are the selectivities $S_A$, $S_{AA}$ and $S_{DP}$ at the reaction tube exit and $STY_{DP}$ is the space time yield of the desired product at the reaction tube exit.

TABLE 1

| Propene loading [l(S.T.P.) of propene/l · h] | $T_A$ [° C.] | $T_B$ [° C.] | $C_{PA}$ (%) | $C_{PE}$ (%) | $S_{AE}$ (%) | $S_{AAE}$ (%) | $S_{DPE}$ (%) | $STY_{DP}$ (g/l · h) |
|---|---|---|---|---|---|---|---|---|
| 100 | 312 | 312 | 76.9 | 94.6 | 91.82 | 4.44 | 96.3 | 230.8 |
| 125 | 316 | 316 | 78.2 | 94.1 | 92.73 | 5.09 | 97.8 | 292.2 |
| 175 | 325 | 336 | 76.3 | 94.9 | 90.07 | 7.34 | 97.4 | 413.5 |
| 175 | 320 | 341 | 72.1 | 95.0 | 90.13 | 7.24 | 97.4 | 474.2 |
| 200 | 325 | 346 | 73.7 | 94.5 | 90.65 | 7.49 | 98.1 | 468.8 |

If the propene loading is increased <200 l(S.T.P.) of propene/l·h, the results shown in Table 2 are obtained. Table 2 additionally shows the conditions to be established for a comparative experiment at 200° C.

TABLE 2

| Propene loading [l(S.T.P.) of propene/l · h] | $T_A$ [° C.] | $T_B$ [° C.] | $C_{PA}$ (%) | $C_{PE}$ (%) | $S_{AE}$ (%) | $S_{AAE}$ (%) | $S_{DPE}$ (%) | $STY_{DP}$ (g/l · h) |
|---|---|---|---|---|---|---|---|---|
| 225 | 325 | 357 | 72.4 | 94.5 | 89.22 | 7.88 | 97.1 | 528.6 |
| 250 | 330 | 361 | 72.3 | 94.5 | 88.84 | 8.07 | 96.91 | 586.5 |
| 200 (Comparative experiment) | 300 | 370 | 44 | 94.5 | 88.2 | 8.5 | 96.7 | 468.8 |

We claim:

1. A process for the catalytic gas-phase oxidation of propene to acrolein, in which a reaction gas starting mixture comprising propene, molecular oxygen and at least one inert gas, at least 20% by volume of which consists of molecular nitrogen, and containing the molecular oxygen and the propene in a molar ratio $O_2:C_3H_6$ of $\geq 1$ is passed, at elevated temperatures, over a fixed-bed catalyst, whose active material is at least one molybdenum- and/or tungsten- and bismuth-, tellurium-, antimony-, tin- and/or copper-containing multimetal oxide, in such a way that the propene conversion in a single pass is $\geq 90$ mol % and the associated selectivity of the acrolein formation and of the acrylic acid byproduct formation together is $\geq 90$ mol %, wherein a) the loading of the fixed-bed catalyst with the propene contained in the reaction gas starting mixture is $\geq 160$ l(S.T.P.) of propene per l of catalyst bed per h,
   b) the fixed-bed catalyst consists of a catalyst bed arranged in two spatially successive reaction zones A, B, the temperature of the reaction zone A being from 300 to 390° C. and the temperature of the reaction zone B being from 305 to 420° C. and at the same time being at least 50° C. above the temperature of the reaction zone A,
   c) the reaction gas starting mixture flows first through the reaction zone A and then through the reaction zone B and
   d) the reaction zone A extends to a propene conversion of from 40 to 80 mol %.

2. A process as claimed in claim 1, wherein the reaction zone A extends to a propene conversion of from 50 to 70 mol %.

3. A process as claimed in claim 1, wherein the reaction zone A extends to a propene conversion of from 65 to 75 mol %.

4. A process as claimed in claim 1, wherein the temperature of the reaction zone B is at least 10° C. above the temperature of the reaction zone A.

5. A process as claimed in 1, wherein the temperature of the reaction zone B is from 305 to 340° C.

6. A process as claimed in claim 1, wherein the temperature of the reaction zone B is from 310 to 330° C.

7. A process as claimed in claim 1, wherein the propene conversion in a single pass is $\geq 94$ mol %.

8. A process as claimed in claim 1, wherein the selectivity of the acrolein formation and of the formation of acrylic acid byproduct together is $\geq 94$ mol %.

9. A process as claimed in claim 1, wherein the propene loading of the catalyst bed is $\geq 165$ l (S.T.P.)/l·h.

10. A process as claimed in claim 1, wherein the propene loading of the catalyst bed is $\geq 170$ l (S.T.P.)/l·h.

11. A process as claimed in claim 1, wherein the one or more inert gases comprise $\geq 40\%$ by volume of molecular nitrogen.

12. A process as claimed in claim 1, wherein the one or more inert gases comprise $\geq 60\%$ by volume of molecular nitrogen.

13. A process as claimed in claim 1, wherein the one or more inert gases comprise steam.

14. A process as claimed in claim 1, wherein the one or more inert gases comprise $CO_2$ and/or CO.

15. A process as claimed in claim 1, which is carried out at an operating pressure of from 0.5 to 3.5 bar.

16. A process as claimed in claim 1, wherein the molar $O_2:C_3H_6$ ratio in the reaction gas starting mixture is from 1.5 to 2.0.

17. A process as claimed in claim 1, wherein air is concomitantly used as the oxygen source.

18. A process as claimed in claim 1, wherein the propene content of the reaction gas starting mixture is from 4 to 15% by volume.

19. A process as claimed in claim 1, wherein the propene content of the reaction gas starting mixture is from 5 to 12% by volume.

20. A process as claimed in claim 1, wherein the propene content of the reaction gas starting mixture is from 5 to 8% by volume.

21. A process as claimed in claim 1, wherein the active material of the fixed-bed catalyst is at least one multimetal oxide of the formula I $$Mo_{12}Bi_aFe_bX^1_cX^2_dX^3_eX^4_fO_n \quad (1)$$

where $X^1$ is nickel and/or cobalt, $X^2$ is thallium, an alkali metal and/or an alkaline earth metal, $X^3$ is zinc, phosphorus, arsenic, boron, antimony, tin, cerium, lead and/or tungsten, $X^4$ is silicon, aluminum, titanium and/or zirconium, a is from 0.5 to 5, b is from 0.01 to 5, c is from 0 to 10, d is from 0 to 2, e is from 0 to 8, f is from 0 to 10 and n is a number which is determined by the valency and frequency of the elements in I other than oxygen.

22. A process as claimed in claim 1, wherein the active material of the fixed-bed catalyst is at least one multimetal oxide of the formula II $$[Y^1_{a'}Y^2_{b'}O_{x'}]_p[Y^3_{c'}Y^4_{d'}Y^5_{e'}Y^6_{f'}Y^7_{g'}Y^2_{h'}Y^7_{g'}Y^2_{h'}O^7_{y'}]_q \quad (II),$$

where $Y^1$ is bismuth, tellurium, antimony, tin and/or copper, $Y^2$ is molybdenum and/or tungsten, $Y^3$ is an alkali metal, thallium and/or samarium, $Y^4$ is an alkaline earth metal, nickel, cobalt, copper, manganese, zinc, tin, cadmium and/or mercury, $Y^5$ is iron, chromium, cerium and/or vanadium, $Y^6$ is phosphorus, arsenic, boron and/or antimony, $Y^7$ is a rare earth metal, titanium, zirconium, niobium, tantalum, rhenium, ruthenium, rhodium, silver, gold, aluminum, gallium, indium, silicon, germanium, lead, thorium and/or uranium, a' is from 0.01 to 8, b' is from 0.1 to 30, c' is from 0 to 4, d' is from 0 to 20, e' is from 0 to 20, f' is from 0 to 6, g' is from 0 to 15, h' is from 8 to 16, x' and y' are numbers determined by the valency and frequency of the elements in II other than oxygen and p and q are numbers whose ratio p/q is from 0.1 to 10, containing three-dimensional regions of the chemical composition $Y^1_{a'}, Y^2_{b'}, O_{x'}$, which are delimited from their local environment owing to their composition differing from their local environment and whose maximum diameters are from 1 nm to 100 μm.

23. A process as claimed in claim 1, wherein the catalyst bed comprises annular and/or spherical catalysts.

24. A process as claimed in claim 23, wherein the ring geometry is the following:

external diameter: from 2 to 10 mm, length: from 2 to 10 mm, wall thickness: from 1 to 3 mm.

25. A process as claimed in claim 23, wherein the spherical catalyst is a coated catalyst consisting of a spherical carrier (from 1 to 8 mm diameter) and a coat (from 10 to 1000 μm thick) comprising active material and applied to said carrier.

26. A process as claimed in claim 1, which is carried out in a two-zone tube-bundle reactor.

27. A process for the preparation of acrylic acid, which comprises a process as claimed in claim 1.

* * * * *

UNITED STATES PATENT AND TRADEMARK OFFICE
CERTIFICATE OF CORRECTION

PATENT NO.    : 6,395,936 B1  
DATED         : May 28, 2002  
INVENTOR(S)   : Heiko Arnold et al.

Page 1 of 1

It is certified that error appears in the above-identified patent and that said Letters Patent is hereby corrected as shown below:

<u>Column 3,</u>  
Line 46, "4200°" should read -- 420° --.  
Line 60, "3300°" should read -- 330° --.

<u>Column 15,</u>  
Line 51, "50°" should read -- 5° --.

Signed and Sealed this

Eighteenth Day of October, 2005

JON W. DUDAS  
*Director of the United States Patent and Trademark Office*